United States Patent

Sasso, Jr.

[11] Patent Number: 5,603,315
[45] Date of Patent: Feb. 18, 1997

[54] MULTIPLE MODE OXYGEN DELIVERY SYSTEM

[75] Inventor: Richard E. Sasso, Jr., South Russell, Ohio

[73] Assignee: Reliable Engineering, S. Russell, Ohio

[21] Appl. No.: 514,675

[22] Filed: Aug. 14, 1995

[51] Int. Cl.$^6$ ................................................ A61M 16/00
[52] U.S. Cl. ........................... 128/204.18; 128/204.21; 128/204.23; 128/207.18; 128/204.26; 128/202.22
[58] Field of Search .................. 128/207.18, 204.18, 128/204.21, 204.23, 204.26, 202.22

[56] References Cited

U.S. PATENT DOCUMENTS

| | | | |
|---|---|---|---|
| 4,462,398 | 7/1984 | Durkan et al. | 128/200.14 |
| 4,498,471 | 2/1985 | Kranz et al. | 128/204.26 |
| 4,584,996 | 4/1986 | Blum | 128/204.21 |
| 4,612,928 | 9/1986 | Tiep et al. | 128/204.23 |
| 4,648,395 | 3/1987 | Sato et al. | 128/204.23 |
| 4,686,974 | 8/1987 | Sato et al. | 128/204.23 |
| 4,686,975 | 8/1987 | Naimon et al. | 128/204.23 |
| 4,744,356 | 5/1988 | Greenwood | 128/204.26 |
| 5,099,837 | 3/1992 | Russel, Sr. et al. | 128/204.26 |
| 5,137,017 | 8/1992 | Salter | 128/207.18 |
| 5,156,145 | 10/1992 | Flood et al. | 128/201.24 |

FOREIGN PATENT DOCUMENTS

| | | | |
|---|---|---|---|
| 2001249 | 1/1979 | United Kingdom | 128/202.22 |
| 2001537 | 2/1979 | United Kingdom | 128/202.22 |

Primary Examiner—Aaron J. Lewis
Assistant Examiner—Eric P. Raciti
Attorney, Agent, or Firm—Oldham & Oldham. Co., LPA

[57] ABSTRACT

In various embodiments of a pulse dose and conservation oxygen delivery system, a control circuit, which is typically microprocessor based, monitors a differential pressure sensor coupled to a patient interface such as a cannula or a face mask. When a patient inhales, a negative pressure is detected at the patient interface point. This condition is sensed and an electrical signal corresponding to the condition is sent to the control circuit. The control circuit processes the signal and then energizes a valve, through driver circuitry, that connects the patient to the oxygen supply for a fixed period of time at a preselected amount. The control circuit continually monitors the pressure differentials at the patient interface and only delivers pulses of oxygen upon the inhalation of the patient. Oxygen delivery is based on a fixed volume of oxygen per breath which provides the advantage of a varying net volume being delivered to the patient per period of time depending on their respiratory rate. If a patient exercises and their breathing rate increases, the control circuit will automatically and proportional to the breathing rate, increase the net volume of oxygen being delivered. In addition if the control circuit fails to sense patient inhalation for a predetermined period of time, it will automatically force pulses of oxygen to the patient while signalling this emergency condition to others. If the control circuit malfunctions or the unit loses power it will fail in such a way that it will still supply a continuous flow of oxygen to the patient, providing an extra level of safety.

34 Claims, 13 Drawing Sheets

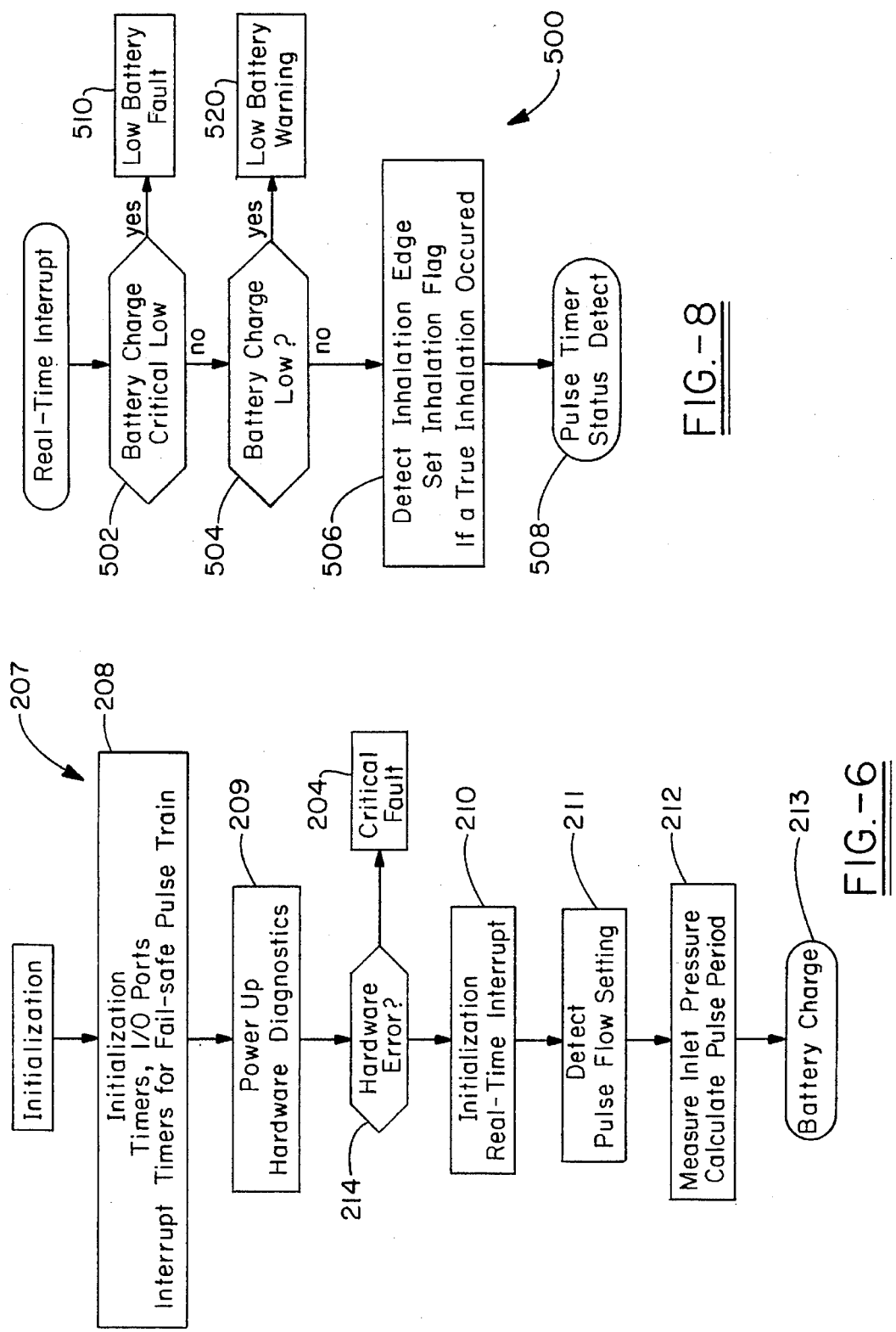

MULTIPLE MODE OXYGEN DELIVERY SYSTEM

TECHNICAL FIELD

This invention relates to an oxygen delivery apparatus and method for operating the same. This invention relates particularly to pulse dose and conservation delivery of oxygen in accurate amounts as would be prescribe by a physician.

BACKGROUND

Oxygen delivery systems have been developed for providing supplemental oxygen therapy for a variety of diseases or conditions, such as chronic obstructive pulmonary disease (COPD), respiratory conditions or other medical conditions which require increased oxygen supply to the patient. Supplemental oxygen therapy can be provided using stationary liquid oxygen systems which require a patient to remain stationary during the therapy, which may be required for extended periods of time. Although providing desired therapeutic characteristics, such approaches are undesirable, because they do not allow a patient to have freedom of travel and to function relatively normally. There thus have been developed portable oxygen systems, using small lightweight cylinders of oxygen gas, with offering ambulatory oxygen patients an improve alternative to stationary liquid oxygen systems. Historically, in such portable oxygen systems, oxygen has been supplied to medical patients in a continuous flow, usually administered with cannula or a face mask. Because the human body only needs oxygen during the inhalation phase of the respiratory cycle, oxygen is wasted during the exhalation cycle. This waste of oxygen was also a problem for emergency medical personnel. Ambulatory services were forced to carry larger oxygen tanks that took up limited space and had to be replenished more often. This took time and forced health care professionals to incur unnecessary costs, which in the end were passed on to the patient. In addition, constant exposure to the flow of oxygen tends to dry a patient's nasal passages, causing discomfort and irritation. Due to this, prior art devices were required to humidify the oxygen before it was delivered to the patient which required additional steps and mechanisms at additional costs.

Because of these deficiencies, oxygen conservation devices were developed which deliver oxygen only during the inhalation phase of the respiratory cycle. Generally, these devices function by opening an oxygen supply valve during inhalation and closing the valve during exhalation. These devices drastically reduced the amount of wasted oxygen which meant that smaller, more lightweight tanks could be used.

One important deficiency that still exists in the prior art is that oxygen pressure is assumed to be constant. A high pressure tank of oxygen is fed to a pressure regulator usually designed to output a fixed pressure, typically 20 psi or 50 psi. As the oxygen is depleted from the tank, its pressure will decrease and these fluctuations coupled with less than accurate characteristics of most regulators, results in patients not receiving exact prescribed amounts of oxygen. In addition, calibration of prior art devices is based on the output of the pressure regulator, either 20 psi or 50 psi. Different pressure regulators are not interchangeable without modification to the oxygen delivery controls.

Also in known oxygen delivery systems, a problem has existed in that if the pressure regulator or other components of the delivery system fail, oxygen may not be properly supplied to the patient as required. Such an occurrence could result in a dangerous condition, as the oxygen supply to the patient may be cutoff or may be inadequate for providing the prescribed rate of oxygen required by the patient.

Thus, based upon the foregoing, the performance of oxygen conservation devices or pulse does devices are generally limited by the performance of the available pressure regulators used as a part thereof. As an example, a typical pressure regulator may be a diaphragm regulator, which will regulate oxygen supply within a tolerance band of the regulator, with the output pressure of the regulator affecting the flow rate of oxygen proportionally, such that the supply of oxygen is not constant and precise according to a prescribed oxygen requirement for a particular patient. In the example of a diaphragm regulator, the regulated pressure output may be selected to be 20 psi, with the actual amount of oxygen delivered varying between 17 psi to 23 psi assuming a plus or minus 15% tolerance in the regulator. In such an example, if a patient is prescribed 5 L/min. of oxygen, the patient may receive anywhere between 4 L/min. to 6 L/min. of oxygen, depending on the pressure of the source of compressed oxygen gas. In another aspect, oxygen delivery systems provide a predetermined volume of oxygen per period of time for an inhalation phase of the respiratory cycle. Such an approach assumes that the oxygen required by the patient remains constant, not accounting for changes in the breathing cycle of the patient.

Therefore, in light of the foregoing deficiencies in prior art oxygen delivery systems, a need exists for an oxygen delivery system which can deliver precise doses of oxygen to a patient in a prescribed amount regardless of characteristics of a pressure regulator or changes in the patients respiratory cycle.

SUMMARY OF THE INVENTION

Based upon the foregoing, it is an object of the present invention is to provide a pulse dose or conservation oxygen delivery system and method of operating the same wherein oxygen pressure is continually adjusted to provide an accurate output despite inaccuracies induced by conventional regulators and pressure changes due to oxygen tank consumption.

Another object of this invention is to conserve oxygen by supplying it during the inhalation phase of breathing and not during the exhalation phase. Demand is triggered by a patient beginning the inhalation phase. This conservation may be further enhanced by only delivering doses of oxygen during the first half of the inhalation cycle.

A further object of this invention is to provide a fail safe feature that will function irrespective of a malfunction in any electronic or mechanical controls. If the pulse dose delivery control malfunctions, oxygen will be continuously delivered to the patient at a prescription rate or other predetermined rate. If the oxygen delivery system malfunctions altogether, the invention also provides supply valves which will fail in a fashion that will allow for a continuous flow of oxygen.

Yet a further object of this invention is to detect if a patient stops breathing for a predetermined amount of time and if so, force pulses of oxygen to the patient while signalling medical personnel through a series of audible, visual or other alarms, either locally or remotely.

Another objective is to reduce the weight and size of the oxygen supply apparatus while increasing the length of time it can operate thus providing the patient with significantly more freedom to travel and function normally in society.

In the present invention, various embodiments of pulse dose and conservation oxygen delivery systems are provided which overcome the deficiencies in the prior art respiratory gas delivery systems. In the preferred embodiment, the respiratory gas delivery system includes a control circuit, which is typically microprocessor based, monitors a differential pressure sensor coupled to a patient interface such as a cannula or a face mask. When a patient inhales, a negative pressure is detected at the patient interface point. This condition is sensed and an electrical signal corresponding to the condition is sent to the control circuit. The control circuit processes the signal and then energizes a valve, through driver circuitry, that connects the patient to the oxygen supply for a fixed period of time at a preselected amount. The control circuit continually monitors the pressure differentials at the patient interface and only delivers pulses of oxygen upon inhalation of the patient. Oxygen delivery is based on a fixed volume of oxygen per breath which provides the advantage of a varying net volume being delivered to the patient per period of time depending on and proportional to their respiratory rate. Thus, if a patient exercises and their breathing rate increases, the control circuit will automatically and proportional to the breathing rate, increase the net volume of oxygen being delivered. In addition if the control circuit fails to sense patient inhalation for a predetermined period of time, it will automatically force pulses of oxygen to the patient while signalling this emergency condition to others. Further, if the control circuit malfunctions or the unit loses power it will fail in such a way that it will still supply a continuous flow of oxygen to the patient, providing an extra level of safety.

BRIEF DESCRIPTION OF THE DRAWINGS

The above objects and advantages of the present invention will become more readily apparent from a reading of the detailed description of preferred embodiments taken in conjunction with the drawings, wherein:

FIG. 6 is a flow chart of the microprocessor control circuit INITIALIZATION subroutine.

FIG. 8 is a flow chart of the microprocessor control circuit REAL TIME INTERRUPT routine.

DETAILED DESCRIPTION OF THE INVENTION

Figure 1:
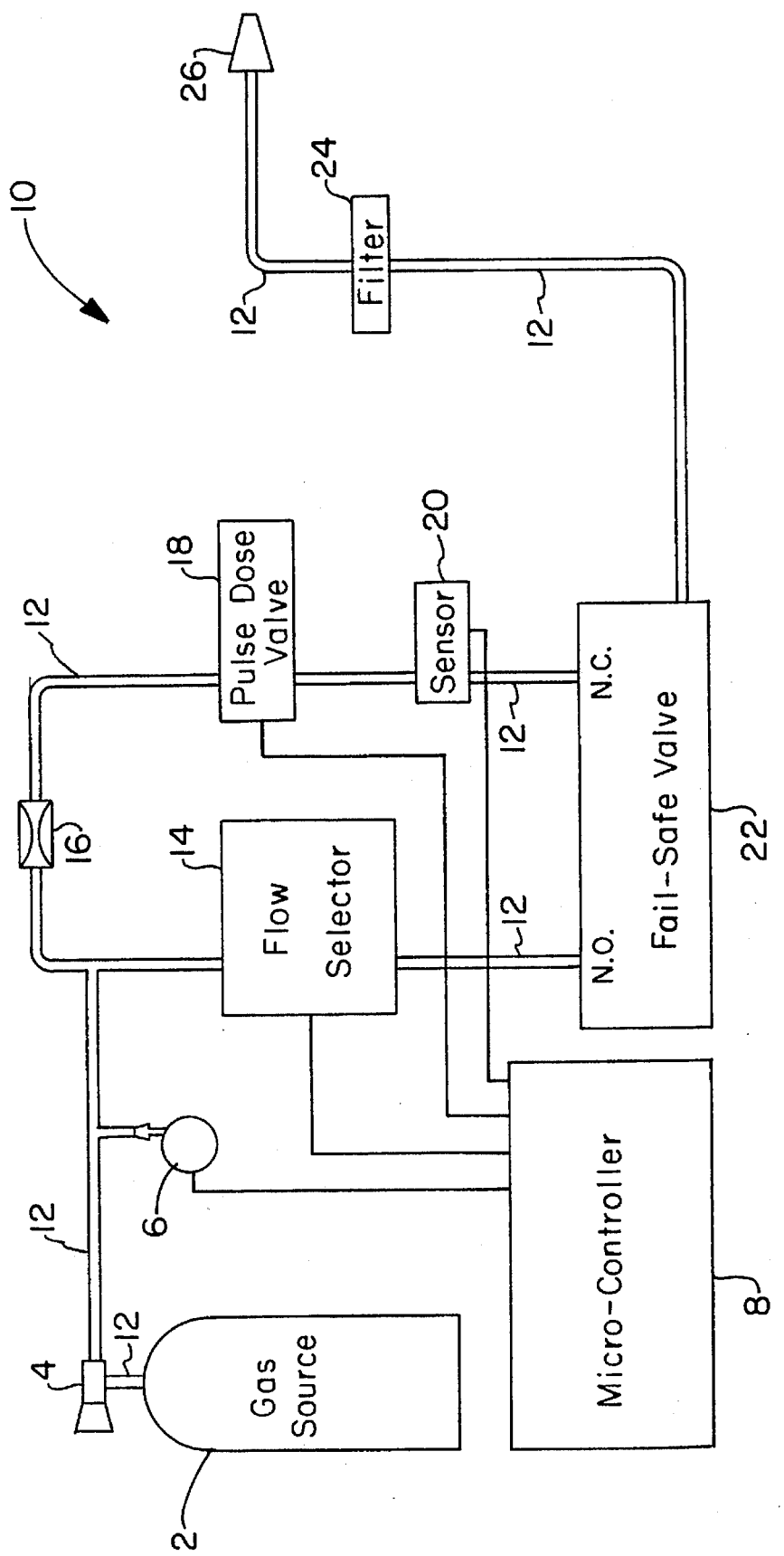
FIG. 1 is a simplified block diagram of the pulse dose and conservation oxygen delivery system in a general embodiment.

The pulse dose and conservation oxygen delivery apparatus 10 of the present invention is depicted in FIG. 1 in a simplified format. The apparatus 10 is supplied by oxygen source 2 which could be a wall supply, a compressor or a portable tank. This last option is preferable because one object of the invention is that it be highly portable in order to provide patients with as much freedom as possible. Oxygen source 2 is then coupled by line 12 to pressure regulator 4 in order to decrease the high pressure of oxygen source 2 to a lower, more manageable pressure. As used herein, any fluid conveying means, such as a duct, pipe, channel, or other closed fluid conduit, is referred to as a line. Many types of regulators could be used such as diaphragm or piston types.

Figure 2:
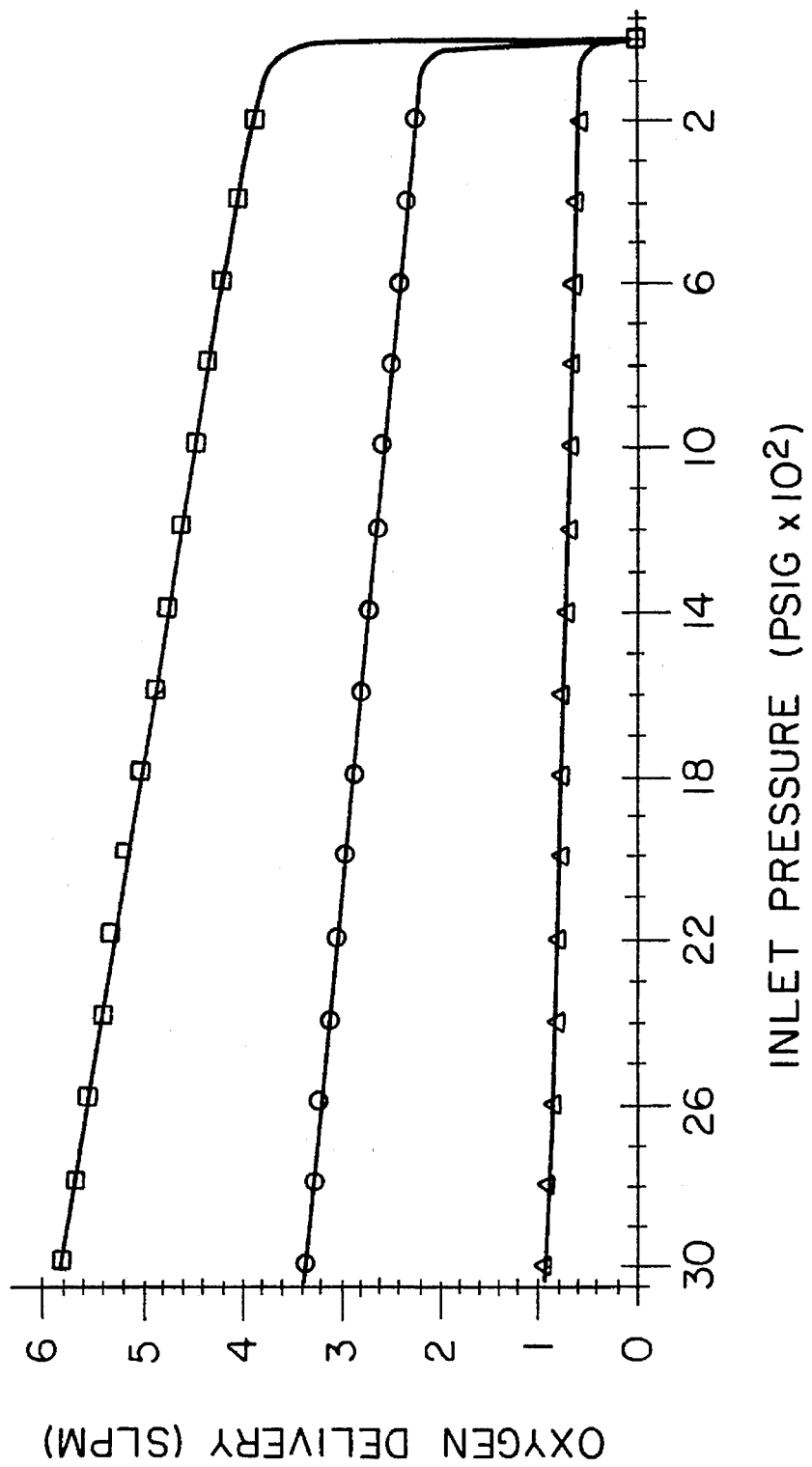
FIG. 2 is a chart depicting the flow regulation curve of a piston type oxygen pressure regulator.

Typical output pressures used in patient oxygen therapy systems are 20 psi and 50 psi. As will be explained, in the present invention, other regulator output pressures can be used including nonstandard and variable values. Prior art devices were limited due to being designed around a particular oxygen source's output pressure. In the present invention, the output from pressure regulator 4 is constantly monitored by processing unit, such as a micro-controller 8 via feedback from a transducer. The need for this constant monitoring is demonstrated by FIG. 2 which represents a flow regulation curve showing the output flow of oxygen from a pressure regulator, in this case a piston type, as the inlet pressure to the regulator decreases. This decrease in pressure is associated with the contents of a tank being consumed. As shown in FIG. 2, it should be understood that as the inlet pressure decreases, the output pressure also decreases linearly until an end point is reached at which output pressure falls off sharply. This curve demonstrates the need for constant pressure regulator output monitoring.

In FIG. 1, the transducer is represented by a pressure sensor 6 which is coupled by a line 12 coming from the output of the pressure regulator 4. In this embodiment, the pressure sensor 6 provides feedback to the micro-controller 8 as to what the pressure regulator's 4 actual measured output value is in psi. Line 12 further connects pressure regulator 4 in series with flow selector 14. Flow selector 14 receives pressurized oxygen and based on its calibration or settings, outputs a volume of oxygen in liters per minute. Flow selector 14 may be an electro-mechanical device that may be adjusted by a mechanical switch or a potentiometer. It could also be adjusted via the micro-controller 8 with corresponding feedback.

Also coupled by line 12 to pressure regulator 4 is restrictor 16, pulse dose valve 18, and flow sensor 20 all in series with each other. Restrictor 16 is a mechanical device which passively limits oxygen passing through at a predetermined maximum pressure. In the embodiment depicted in FIG. 1, restrictor 16 can limit oxygen throughput to approximately 15 L/min. as an example. Restrictor 16 serves as a fail safe mechanism because it is in series with the fail safe oxygen supply path and can limit oxygen pressure to reasonably safe levels without any external power requirements. Pulse dose valve 18 is controlled by micro-controller 8 which controls the valve paths to allow oxygen to flow to the patient during the inhalation phase of breathing and not during the patient's exhalation phase. Flow sensor 20 allows the micro-controller to determine which breathing phase the patient is in by detecting pressure changes due to inhalation and exhalation. Both oxygen outputs from flow selector 14 and flow sensor 20 are input to fail-safe valve 22, which then is coupled in series by line 12 to bacteria filter 24, and then further coupled to the patient via output port 26. Output port 26 may be connected to a cannula that is inserted into the patient's airway or a face mask that is worn over the patient's nose and mouth for example. Although the preferred embodiments herein show coupling of various components through the feed through line 12, should be understood that the particular arrangement of these components could change.

Figure 3:
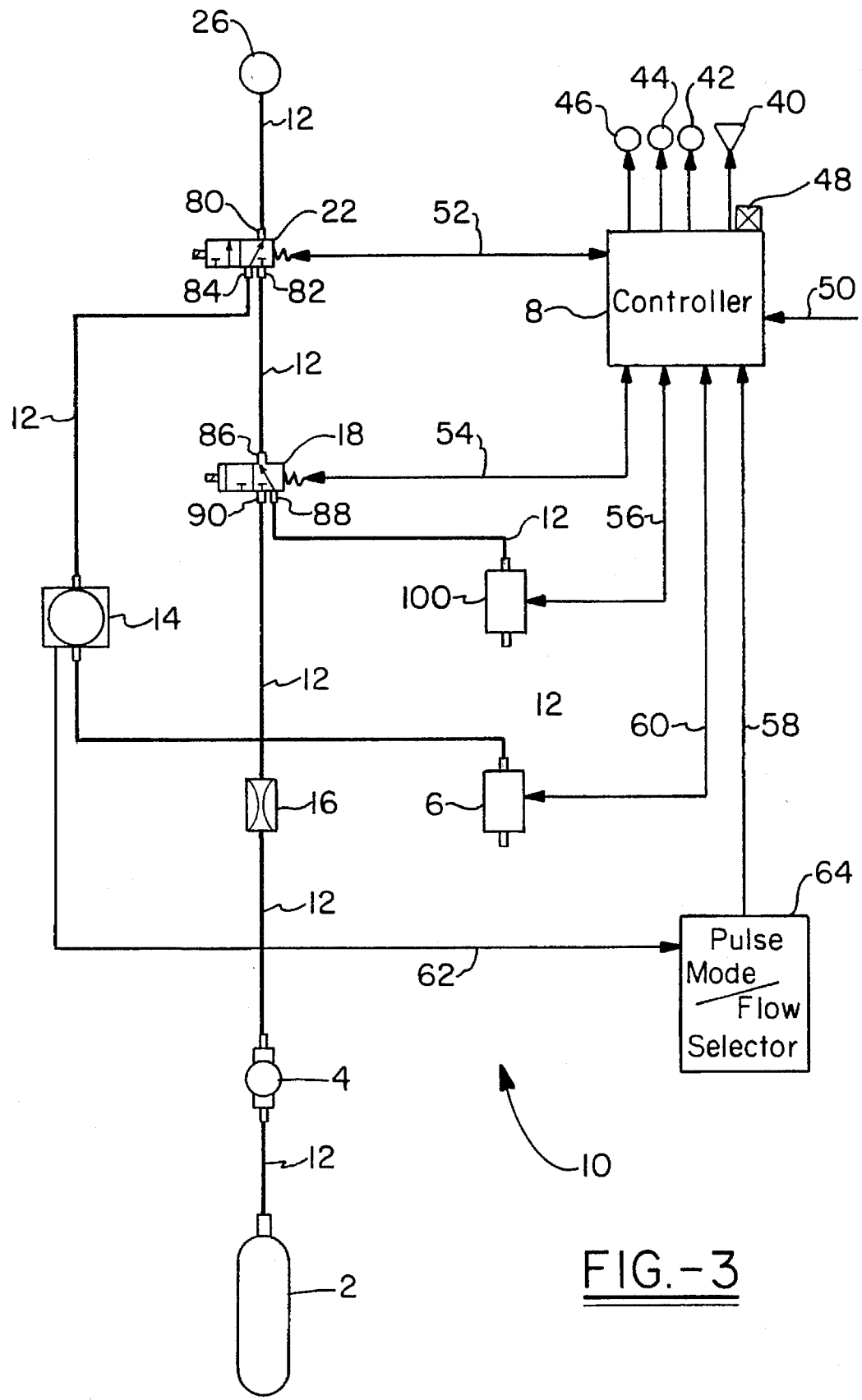
FIG. 3 is a block diagram of the complete pulse dose and conservation oxygen delivery system.

A more detailed block diagram of a first embodiment of apparatus 10 is depicted in FIG. 3. Micro-controller 8 monitors and controls all functions of apparatus 10, as discussed previously. Micro-controller 8 could be a conventional computer that is equipped with digital and analog inputs and outputs, memory and other supervisory and control circuitry. The apparatus could also be controlled from a personal computer equipped with interface circuitry. In the preferred embodiment, the micro-controller 8 will be an embedded controller equipped with CMOS integrated circuits which facilitates longer battery life due to low current consumption. One of the main objectives of the invention is to provide patients with a highly portable and long lasting oxygen supply. By decreasing circuit power consumption, smaller, more lightweight batteries can be used while still providing power for prolonged periods of time. Apparatus 10 is supplied electricity via power input 50. Power input 50 could be any standard power source such as a low voltage AC input that is rectified and regulated at the micro-controller board or it could be 120 VAC that is stepped down and then rectified and regulated. Any conventional power source that results in a low voltage direct current supply capable of powering digital electronics would suffice. In the preferred embodiment power input 50 is a lightweight, small rechargeable battery.

Micro-controller 8 has several indicators whereby the patient can monitor how the unit is functioning. For example, there may be an audible alarm 40 which is triggered whenever the patient or someone else needs to be aware of an operating or other condition. Such conditions may comprise sensing when a patient stops breathing, when the micro-controller 8 battery charge becomes too low, when oxygen supply 2 drops below safe levels and a plurality of other conditions. A switch 48 may be selectively actuated to turn off the alarm 40 after a predetermined time if desired.

There may also be provided in conjunction with audible alarm 40, several visual alarms which the user can use to further identify specific problems in operation of the device. While many indicators for every conceivable condition could be used, the preferred embodiment consists of pulse indicator 46, low battery indicator 44 and missing pulse indicator 42. Any type of visual indicator could be used with low-power LED technology being preferred to once again conserve power and decrease the necessary battery size and weight. As previously mentioned, the device is used to monitor breathing of the patient to supply oxygen at the desired time and amount, allowing detection if a patient stops breathing. The apparatus 10 may then include a means to alert desired personnel of such condition, which may again be an audible or other alarm associated with the apparatus 10, or may alternatively be a means to provide communication of such condition to a remote location. For example, the apparatus 10 may include a transmitter for communicating this or another condition through air to a remote receiver, which in turn could alert emergency medical personnel or others.

Also shown in FIG. 3, the patient oxygen output port 26 is connected by line 12 to common port 80 of fail-safe valve 22. Many types of valves could be used such as electronic valves, which must be energized continuously while in one state. Pneumatic valves could also be used but in the preferred embodiment, electronic latching valves are contemplated. This option further enhances the low power consumption of the invention because current is supplied at its peak value only to change the state of the valve with a much lower current used to maintain the latched state. Fail-safe valve 22 is electrically coupled to micro-controller 8 via electrical conductor 52. Although not shown in FIG. 3, it should be understood that power is supplied to all devices, such as valves and pressure transducers, through additional conductors. The normally closed port 82 of fail-safe valve 22 is coupled by line 12 to common port 86 of pulse dose valve 18. Pulse dose valve 18 could also be one of many types common in the art, but again an electronic latching valve is preferred. Conductor 54 couples pulse dose valve 18 to micro-controller 8. Both valves receive electrical signals via their respective conductors directing them to either latch the valve in the normally open position or to release the latch and switch to the normally closed position. If one of the valves is latched in one position, for example the normally open position, then oxygen would pass from the common port through the valve and out the normally open port. If the valve is in the other position then oxygen would flow from the common port and out of the normally closed port. Flow/pressure sensor 100 is coupled to the normally open port 88 of pulse dose valve 18 and electrically coupled to micro-controller 8 via conductor 56.

During normal operation, fail-safe valve 22 will be in its normally closed position and pulse dose valve 18 will be in its normally open position, as controlled by micro-controller 8. In this arrangement, there will be a direct path from patient output port 26 to pressure sensor 100. When the patient begins to inhale, pressure sensor 100 will detect a negative pressure and communicate this to micro-controller 8. Detection of the beginning of the inhalation cycle can be accomplished in many other ways such as replacing pressure sensor 100 with flow sensor 20 as shown in FIG. 1. This arrangement detects when oxygen is pulled through the sensor. The flow sensor could also be repositioned in series with line 12 directly following patient's output port 26 or it could be placed in series between fail-safe valve 22 and pulse dose valve 18, as possible examples. Use of a pressure sensor on line 12 coming off the patient output port 26 is also contemplated. Any arrangement using either a flow sensor or a pressure sensor that enables micro-controller 8 to detect the start of a patients breathing cycle is suitable for the invention. The normally closed port 90 of pulse dose valve 18 is coupled by line 12 through restrictor 16 to pressure regulator 4. Pressure regulator 4 is directly coupled by line 12 to oxygen source 2. As can now be seen, if the apparatus fails or loses power, both the fail-safe valve 22 and the pulse dose valve 18 will default to their normally closed positions. This will provide a direct path of oxygen to patient output port 26 from oxygen source 2. Restrictor 16 will passively limit the amount of oxygen being supplied to the patient at a safe level. This combination allows for an additional level of safety that is necessary with electronic controls. Advanced functions that distinguish this invention from the prior art can be implemented without any sacrifice to the patients safety.

To further implement the novel features of this invention, pressure sensor 6 is connected by line 12 to the output of pressure regulator 4. Pressure sensor 6 supplies feedback to micro-controller 8 via conductor 60. Pressure sensor 6 is used to monitor the actual output pressure from pressure regulator 4. This feature provides significant advantages as most off the shelf pressure regulators are not very accurate as previously described. As an example, a diaphragm regulator of 20 psi, once connected to a cylinder of oxygen, will typically regulate between 17 psi to 23 psi (±15% tolerance) in output pressure. This variance will directly and proportionally affect the flow rate of oxygen to any device that it is coupled to. This means for example, if a patient is prescribed for 5 L/min. of oxygen, the patient may actually receive anything between 4 L/min. to 6 L/min. of oxygen. By monitoring the actual pressure being output by pressure regulator 4 rather than assuming it at the regulators rated value, micro-controller 8 can accurately recalculate the pulse dose needed to comply with a prescribed value for oxygen therapy. This value can literally be recalibrated for each and every breath the patient takes, providing near perfect compliance with the prescribed value.

To provide the patient with oxygen in pulse doses, the operation of the apparatus 10 initiates micro-controller 8 to first calculate the amount that will be provided to the patient. For every flow setting, a base period of time is precalculated and stored in the micro-controller's 8 non-volatile memory. This non-volatile memory preferably may be EEPROM, NOVRAM, FLASH or any other type of technology that will retain values without power. This base period of time will be referred to as the Base Pulse Period or BPP. The BPP is calculated based on pressure within or close to the range of the output pressure of pressure regulator 4. In real time, when the patient is using the device, measurements can be taken during every pause between inhalation cycles when oxygen is not being delivered to the patient or in other intervals if desired. The pressure readings being fed back to micro-controller 8 from pressure sensor 6 are recorded and the difference in the measured pressure and the nominal BPP pressure is used to calculate the Corrected Pulse Period or CPP. With each inhalation taken by the patient, a CPP is calculated and enables micro-controller 8 to switch pulse dose valve 18 to its normally closed port 84, thus supplying oxygen to the patient for a period of time that will deliver the proper fixed volume per breath.

The method of determining the fixed volume of gas per breath will now be discussed further. When a physician prescribes an amount of oxygen for a patient, he will do so at a constant oxygen flow rate (referred to as R2) such that the volume of oxygen needed to be supplied in a breath can be delivered in less than half of the normal inhalation cycle. This is done because only the first half of the inhalation cycle oxygenates the blood. A typical time value for this delivery period is approximately 0.5 seconds (referred to as T1). Once the physician has set apparatus 10 for a specified flow rate and started the unit, micro-controller 8 through pressure sensor 6 will determine the exact pressure output by pressure regulator 4. Micro-controller 8 will next read from its memory the Base Pulse Period value corresponding to the selected flow rate. The Base Pulse Period (referred to as T2) has a duration that at flow rate R2, would deliver at least the same volume of oxygen as would be delivered in a continuous application of oxygen for a duration of T1 at a flow rate less than R2, which will be referred to as R1. At this point, a TER or compensation error period is calculated by taking the difference of P2 (the actual time period of the supplied oxygen) and nominal pressure P1 (period of pulse time theoretically calculated and stored in memory). Depending on the value of this difference, the TER value could be negative or positive. Finally, the Corrected Pulse Period is calculated by adding the TER value to T2. The Corrected Pulse Period is the length of time the pulse dose valve 18 will allow oxygen to flow to the patient during inhalation at an actual pressure regulator 4 output pressure.

If selected by the user, or if electronic malfunctions are detected in the pulse dose features of the invention, apparatus 10 can also function in a continuous mode rather than pulse dose mode. In a continuous mode, fail-safe valve 22 engages to its normally open position and oxygen is supplied continuously at the prescription rate from flow selector 14. This rate is set from remote pulse mode/flow selector 64 which is electrically coupled to flow selector 14 via conductor 62. It is also electrically coupled to micro-controller 8 via conductor 58. Remote pulse mode/flow selector 64 could be a mechanical switch or a variable potentiometer. It is also contemplated that selector 64 is removed and flow selector 14 is preset directly from micro-controller 8 through user input from a keypad or other common selection device known in the art. The continuous mode provides an additional level of safety above that provided by the fail-safe functions. If the unit loses power or completely malfunctions, both valves will default and provide the patient with a continuous supply of oxygen, but it will only be limited by restrictor 16. The supply will greatly exceed the prescription amount. With the continuous mode feature, if micro-controller 8 detects errors only in the pulse dose devices, it can switch to continuous mode which will provide a controlled oxygen flow rate by means of flow selector 14. This also allows for a physician to use the apparatus 10 as a continuous supply if, for medical reasons, he so chooses.

Due to the advanced features of apparatus 10 it also provides further safety for patients by monitoring whether or not they continue to breathe. The method and apparatus may include in the preferred embodiment, the additional feature of monitoring pressure sensor 6 and keeping track of the number of inhalation cycles and the lengths of time between them, allowing micro-controller 8 to calculate the patient's breathing rate. Once this has been calculated, micro-controller 8 may be used to determine the delay (DL1) in which each inhalation should occur. If an inhalation is not sensed within the duration of a different predetermined period (DL2), micro-controller 8 may initiate the necessary sequence of events described earlier to force a pulse of oxygen to the patient. Predetermined period DL2 may be several times greater in time length than DL1, such as a lapse of time equal to several breaths. The pulse of oxygen supplied may also extend for n predetermined number of breathing cycles until n multiplied by DL2 is equal to or larger than DL1. Pulses of oxygen may thus be continuously forced to the patient with only a short delay in between each pulse. During the short delays in pulses, micro-controller 8 through flow/pressure sensor 100 checks to see if the patient has resumed breathing and if so it discontinues the forced pulses. Any detected event where the patient stops breathing may also trigger audible alarm 40 to emit a warning, and missing pulse indicator 42 may be illuminated. Again, the apparatus 10 can also communicate this condition to a remote location. Once the warning condition passes, audible alarm 40 and missing pulse indicator 42 turn off. It is also envisioned as an additional safety feature that even if the missing breath pulse condition passes that the missing pulse indicator 42 would change from a continuously illuminated state to a flashing state. This would allow medical personnel to know that a patient had stopped breathing at some earlier point in time, although the medical personnel were not present. This may provide an important patient diagnostic feature. Although the foregoing features relating to the detection of any breathing cycle events relate to the preferred embodiment, the implementation of monitoring the breathing cycle by other methods is contemplated.

Figure 4:
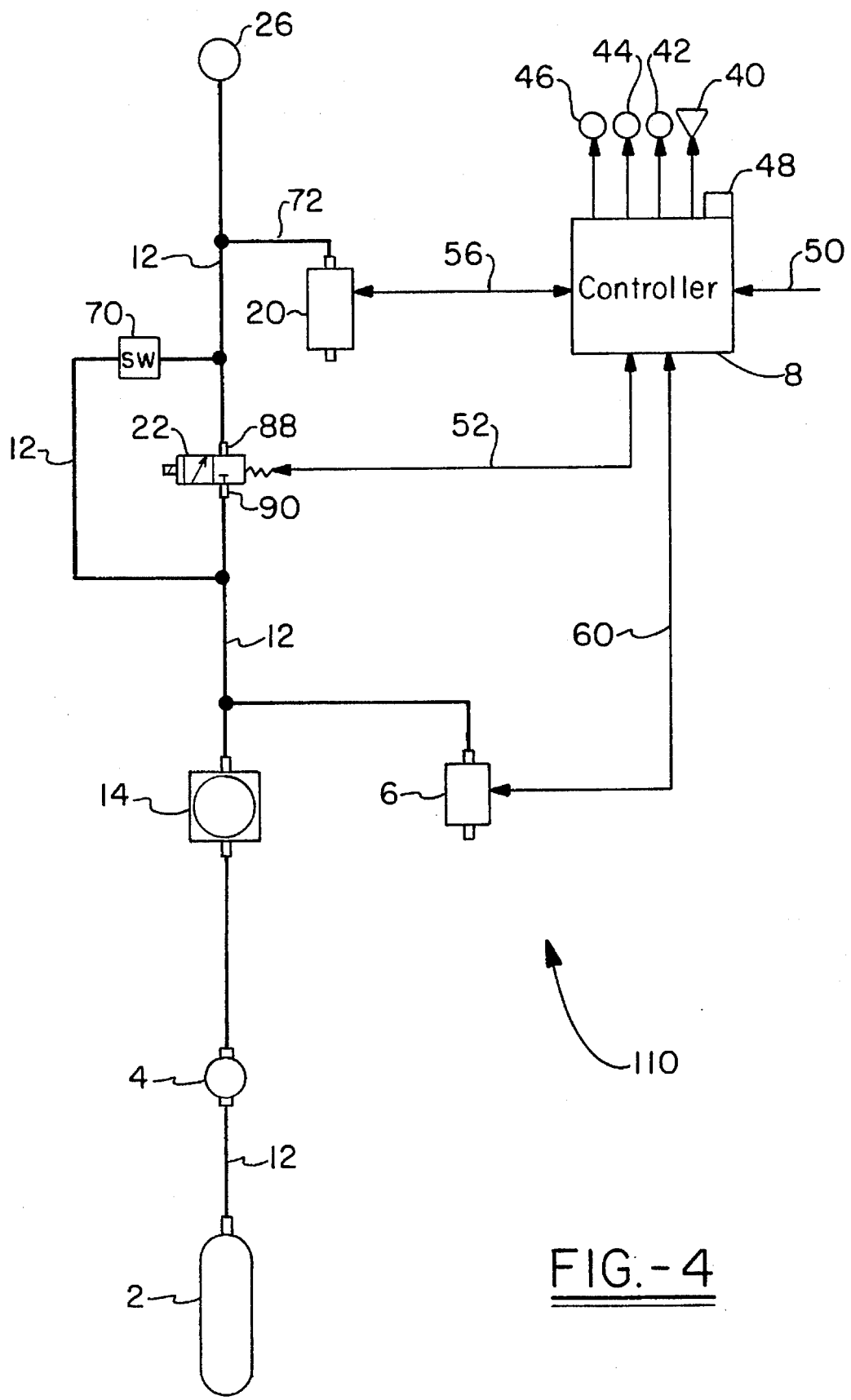
FIG. 4 is a block diagram of an alternate embodiment only disclosing a conservation oxygen delivery system.

FIG. 4 represents a conservation oxygen delivery system 110, being similar to the embodiment of FIG. 3 but without the pulse dose elements. The apparatus 110 functions similar to the description of apparatus 10 in FIG. 3 with regard to detecting the beginning of the patient inhalation phase of breathing. Because there is no pulse dose valve in this embodiment, fail-safe valve 22 is turned on and off by micro-controller 8 to allow for oxygen delivery during inhalation and not during exhalation. Flow selector 14 delivers a preselected prescription rate of oxygen to the patient whenever fail-safe valve 22 is in its normally closed position. In this particular embodiment, continuous supply switch 70 has been added which bypasses fail-safe valve 22 altogether. This allows the device to function as a continuous flow oxygen supply when needed or when wasted consumption is not critical, for example when the device is connected to a compressor or some other virtual source of oxygen. Fail-safe valve 22 will fail in the position which will allow oxygen to flow to the patient if a malfunction should occur. While not disclosed in FIG. 4 as it is in FIG. 3, a restrictor could be used in series with line 12 to limit the pressure at which oxygen would be supplied in the case of a malfunction.

FIG. 4 also shows restrictor 72 between flow/pressure sensor 20 and line 12 connected to patient output port 26. This is used to prevent high pressures from damaging flow/pressure sensor 20 and the same technique could be employed to place maximum pressure delivery limits on other parts of the equipment and patient.

Figure 5:
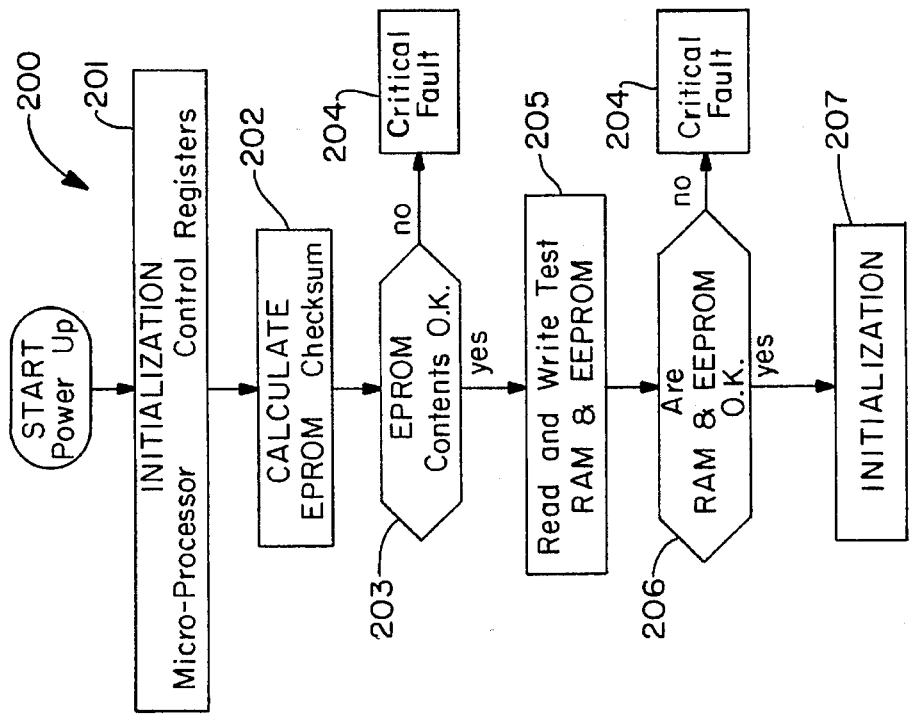
FIG. 5 is a flow chart of the microprocessor control circuit POWER UP subroutine.
Figure 14:
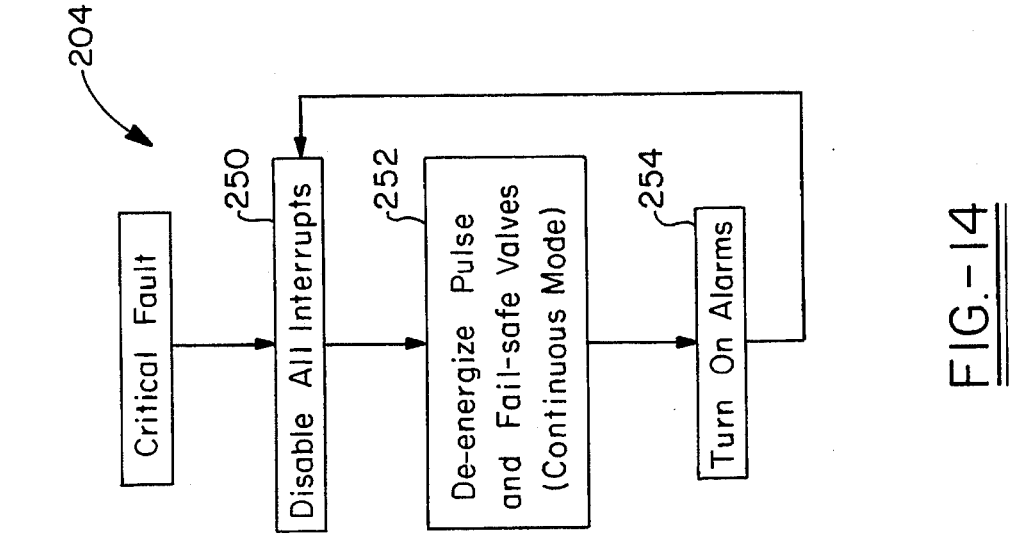
FIG. 14 is a flow chart of the microprocessor control circuit CRITICAL FAULT subroutine.

A significant aspect of the present invention is in its control and monitoring of its devices and the patient, which are all accomplished through micro-controller 8, the operation of which will now be further explained. In the preferred embodiment, when the apparatus has power applied to it by turning it on, micro-controller 8 goes through POWER UP 200 subroutine as shown in FIG. 5. It is to be understood that subroutines will be designated as such by being printed in capital letters. Micro-controller 8 begins by initializing its microprocessor internal control registers 201 which typically aid in memory addressing and basic interface operations. The program memory is then checked for accuracy. Program memory will typically be stored in an EPROM and its checksum value 202 will be calculated and then compared to verify its contents. If after comparing the EPROM contents 203, the value does not verify correctly, CRITICAL FAULT 204 will be executed. When CRITICAL FAULT 204, as shown in FIG. 14, is executed, micro-controller 8 disables all of its interrupts 250 to prevent any further functioning of apparatus 10. It then de-energizes and thereby unlatches both pulse dose valve 18 and fail-safe valve 22 which allows for the continuous flow of oxygen to the patient. Finally, micro-controller 8 turns on alarms 254 and enters an endless loop repeating these steps so that no further operation can take place while the patient is being notified of the malfunction. If the EPROM contents do verify correctly then the next step is to test micro-controller's 8 other memory devices, which may comprise of RAM and EEPROM devices for example. This is done by reading and writing to the memory 205 and then comparing the values to see if they are satisfactory at 206. If they are not then CRITICAL FAULT 204 is called. If the memory verification is successful, then INITIALIZATION 207 is executed.

Figure 12:
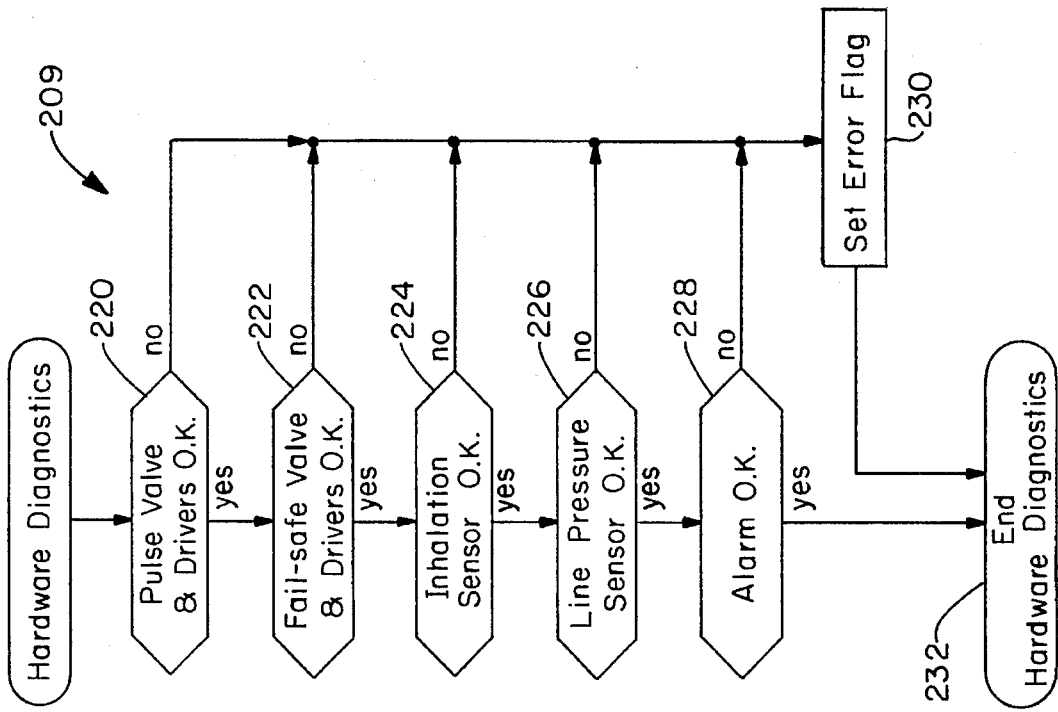
FIG. 12 is a flow chart of the microprocessor control circuit HARDWARE DIAGNOSTICS subroutine.

In FIG. 6, once POWER UP is completed, the microprocessor internal timers, I/O ports, and interrupt timers are all initialized at 208 followed by calling HARDWARE DIAGNOSTICS 209, as shown in FIG. 12. Micro-controller 8 proceeds to test its hardware and if any individual piece fails, an "ERROR" flag 230 is set. In the pulse dose apparatus 10, the pulse dose valve 18 and its driver circuitry is firstly tested at 220, and next fail-safe valve 22 and its driver circuitry is tested at 222. The inhalation sensor which is flow/pressure sensor 100 in FIG. 3 or flow sensor 20 in FIG. 4, is then checked at 224. Pressure sensor 6 is tested at 226 and finally audible alarm 40 is checked at 228. Once all hardware has tested positive or an error flag has been set, the hardware diagnostic routine ends at 232. If a hardware error is reported at 214, then CRITICAL FAULT 204 is entered, wherein program execution will halt and apparatus 10 will default to its fail-safe mode. If no hardware error is detected then it will proceed to initialize its real time interrupt 210, detect the pulse flow setting 211 corresponding to the flow selector 14 and then call MEASURE INLET PRESSURE AND CALCULATE PULSE PERIOD 212. Once this subroutine is completed, BATTERY CHARGE 213 is called.

Figure 19:
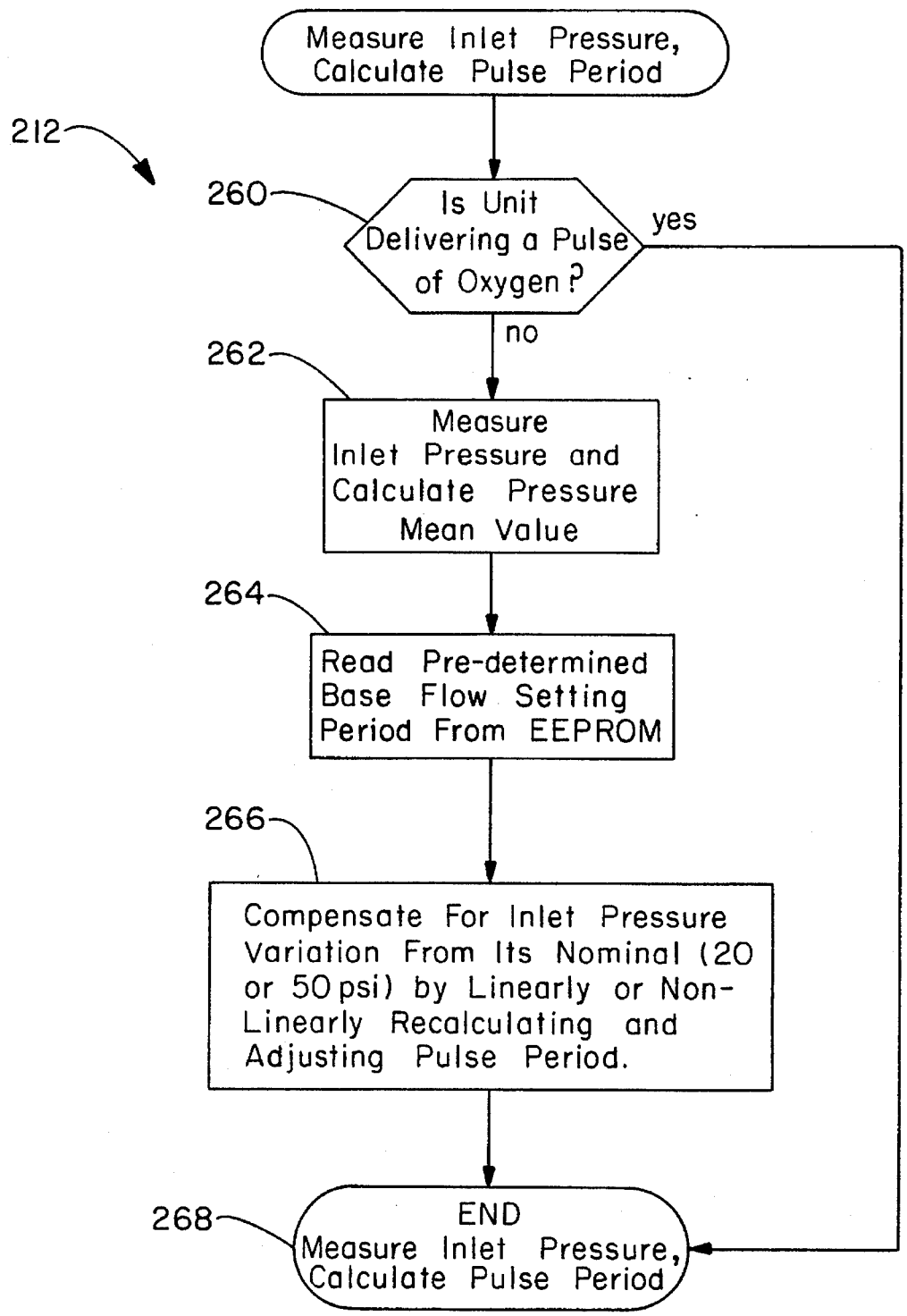
FIG. 19 is a flow chart of the microprocessor control circuit INLET PRESSURE AND CALCULATE PULSE PERIOD subroutine.

MEASURE INLET PRESSURE AND CALCULATE PULSE PERIOD 212, as shown in FIG. 19, begins by determining if apparatus 10 is in the process of delivering a pulse of oxygen at 260. If it is then the subroutine ends at 268. If it is not delivering a pulse of oxygen at 260, the inlet pressure is measured several times by pressure sensor 6 and then its mean value is calculated at 262. The next step is to retrieve the predetermined "Base Pulse Period" value from microcontroller's 8 non-volatile memory at 264. Finally, the "Corrected Pulse Period" is calculated at 266 and the subroutine then returns at 268.

Figure 7:
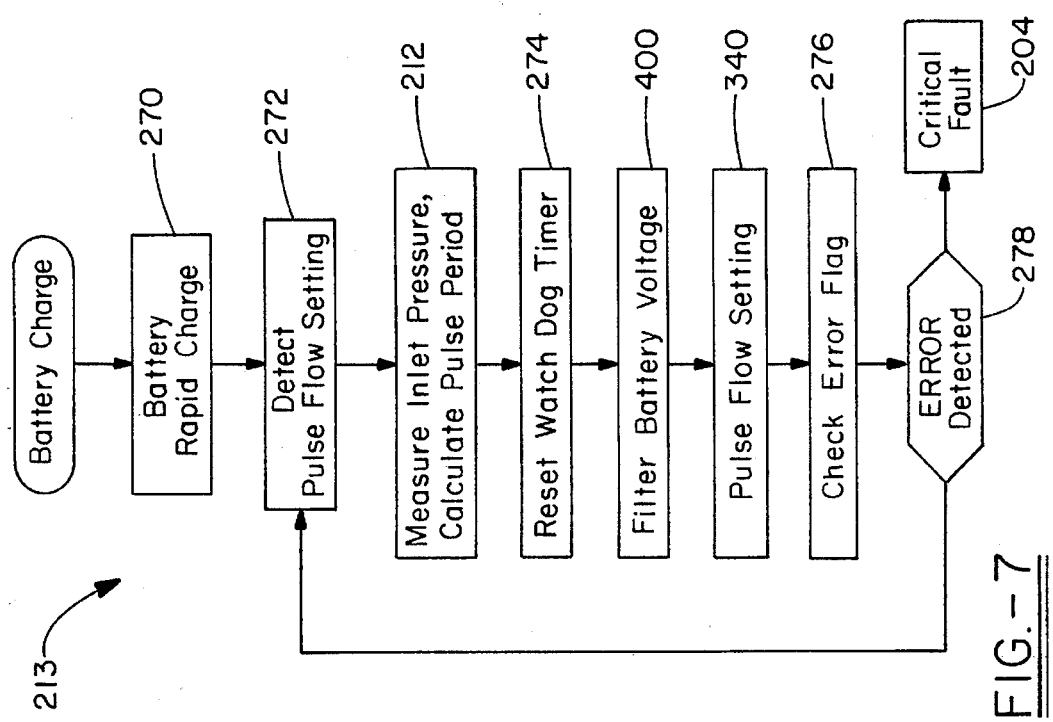
FIG. 7 is a flow chart of the microprocessor control circuit BATTERY CHARGE subroutine.
Figure 13:
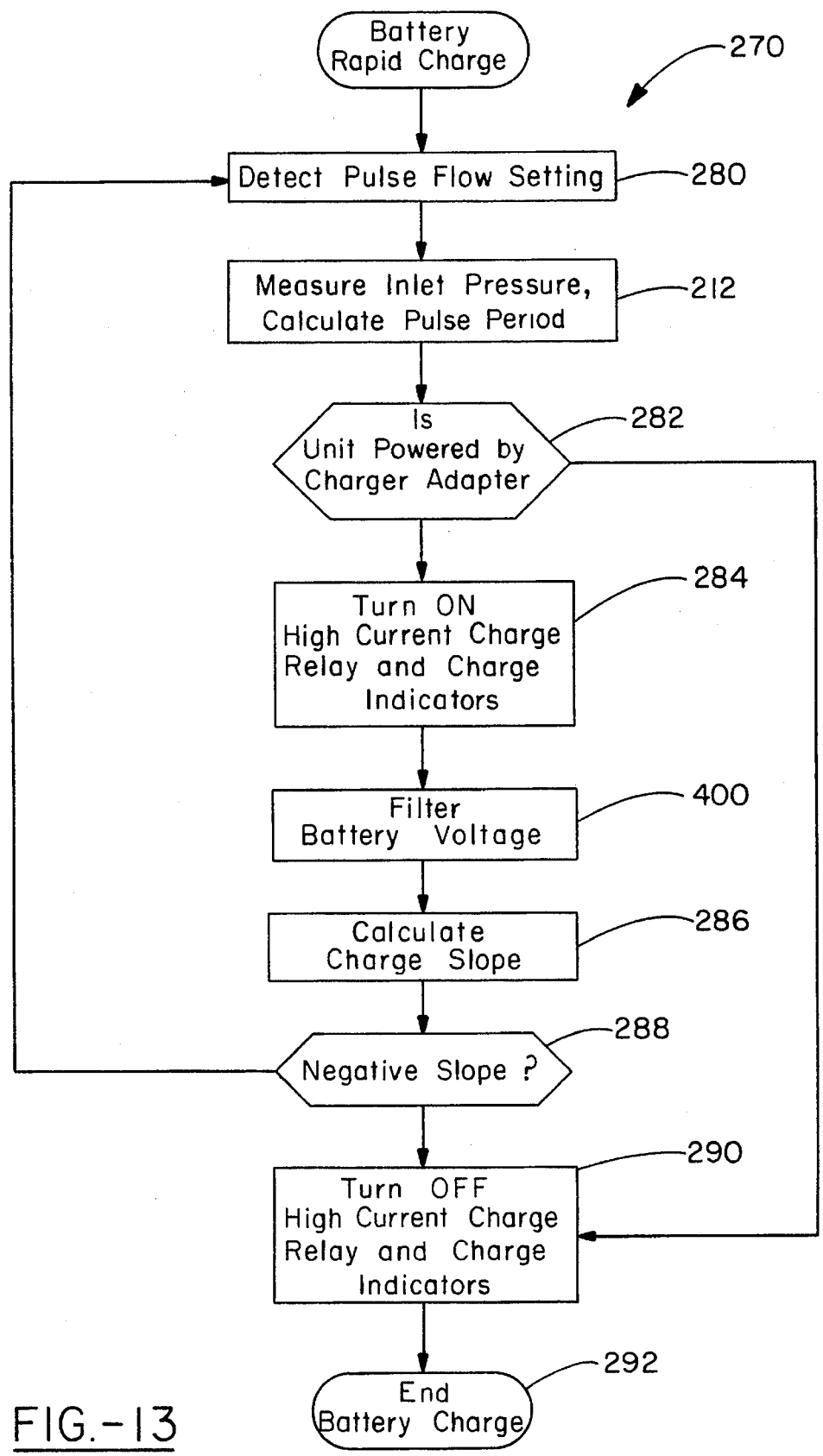
FIG. 13 is a flow chart of the microprocessor control circuit BATTERY RAPID CHARGE subroutine.
Figure 16:
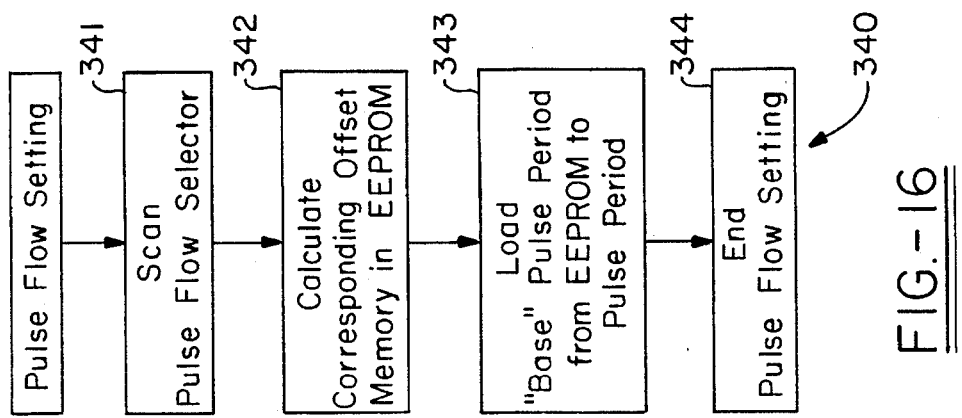
FIG. 16 is a flow chart of the microprocessor control circuit PULSE FLOW SETTING subroutine.
Figure 17:
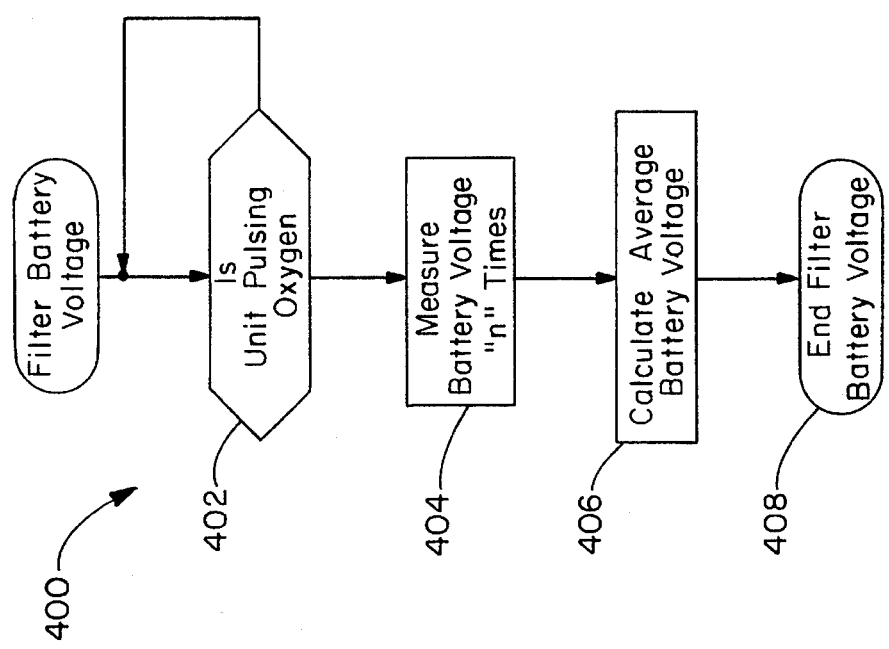
FIG. 17 is a flow chart of the microprocessor control circuit FILTER BATTERY VOLTAGE subroutine.

Next BATTERY CHARGE 213, as shown in FIG. 7, is called which immediately enters BATTERY RAPID CHARGE 270, as shown in FIG. 13. This subroutine begins by reading the pulse dose flow selector 14 setting and then calling MEASURE INLET PRESSURE AND CALCULATE PULSE PERIOD 212, described in FIG. 19. Upon returning from that subroutine micro-controller 8 checks to see if apparatus 10 is being powered by a battery charger/adaptor 282. If not, the unit turns off its high current charge relays 290 to prevent damage to apparatus 10. If it is being powered by a battery charger/adaptor then FILTER BATTERY VOLTAGE 400 is executed, as shown in FIG. 17. This routine simply checks to see if the unit is pulsing oxygen, if not it will continue to check until it is at 402. Once this has been done, micro-controller 8 will measure its battery voltage numerous times at 404 and use those measurements to calculate the average battery voltage at 406. Finally the subroutine will return at 408. Upon returning to BATTERY RAPID CHARGE 270, in FIG. 13, the unit will calculate the charge slope 286 needed to recharge its battery. If the slope is not negative 288, then it will loop to the start and repeat until a negative slope is calculated, which indicates the battery is fully charged. At this point the high current charge relay 290 and indicators will be turned off and the subroutine will end 292. Once back in BATTERY CHARGE 213, micro-controller 8 reads the pulse flow selector reading 272, calls MEASURE INLET PRESSURE AND CALCULATE PULSE PERIOD 212, and resets micro-controller's 8 watch dog timer 274. The watch dog timer is used to make sure the unit is functioning and if not, reset it rather than have it lock up in a continuous faulty loop. The unit then checks its battery by calling FILTER BATTERY VOLTAGE 400, followed by PULSE FLOW SETTING 340, as shown in FIG. 16. PULSE FLOW SETTING 340 begins by determining the setting of the pulse flow selector 341 and then it calculates where in its EEPROM memory the "Base Pulse Period" value is stored 342 and then loads this value into a storage register within the microprocessor 343. It then returns to BATTERY CHARGE 213. Finally micro-controller 8 checks to see if any error flags have been detected at 276. If so CRITICAL FAULT 204 is entered and if not it will loop back and check for the pulse flow selector setting at 272.

Figure 15:
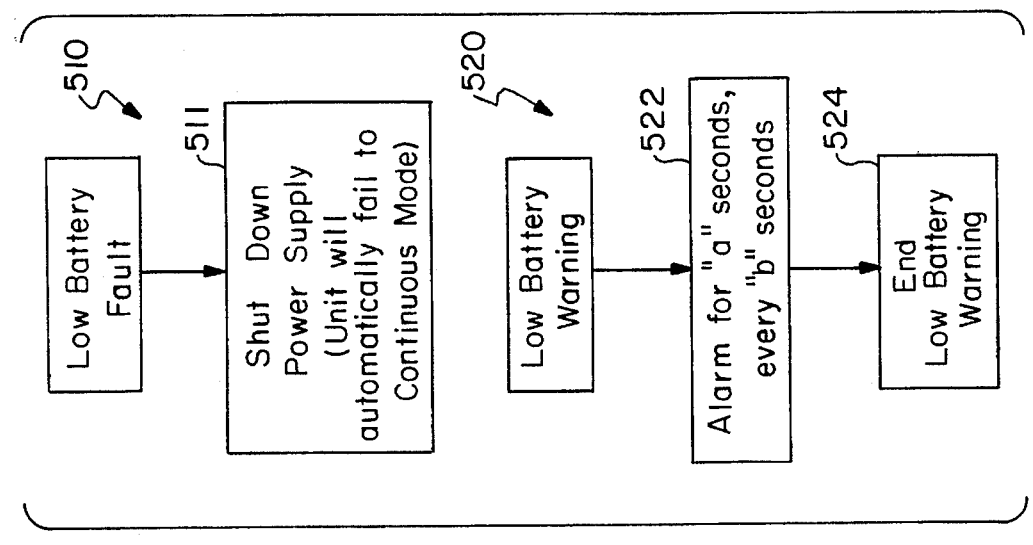
FIG. 15 is a flow chart of the microprocessor control circuit LOW BATTERY FAULT and LOW BATTERY WARNING subroutines.

Upon receiving an interrupt signal from flow/pressure sensor 100 indicating that the patient has begun the inhalation phase of breathing, micro-controller 8 will stop whatever it is currently doing and execute REAL TIME INTERRUPT 500, as shown in FIG. 8. It first checks to see if the battery charge is critically low at 502 and if it is LOW BATTERY FAULT 510 is called. If the battery is not at a critically low charge value, it next determines if the charge is low at 504 even though not critical. If so then LOW BATTERY WARNING 520 is called. If not micro-controller 8 determines whether the real time interrupt was actually caused by the patient beginning inhalation 506 or if it was a false signal. If the signal was accurate, a flag is set in memory pointing this out. After that PULSE TIMER STATUS DETECT 508 is called. LOW BATTERY FAULT 510, in FIG. 15, shuts down all power to the unit causing it to automatically enter the fail-safe mode and continuously supply oxygen to the patient at 511. LOW BATTERY WARNING 520, in FIG. 15, turns on audible alarm 40 for a predetermined length of time and then repeats this several times at 522. It then returns from the subroutine 524.

Figure 9:
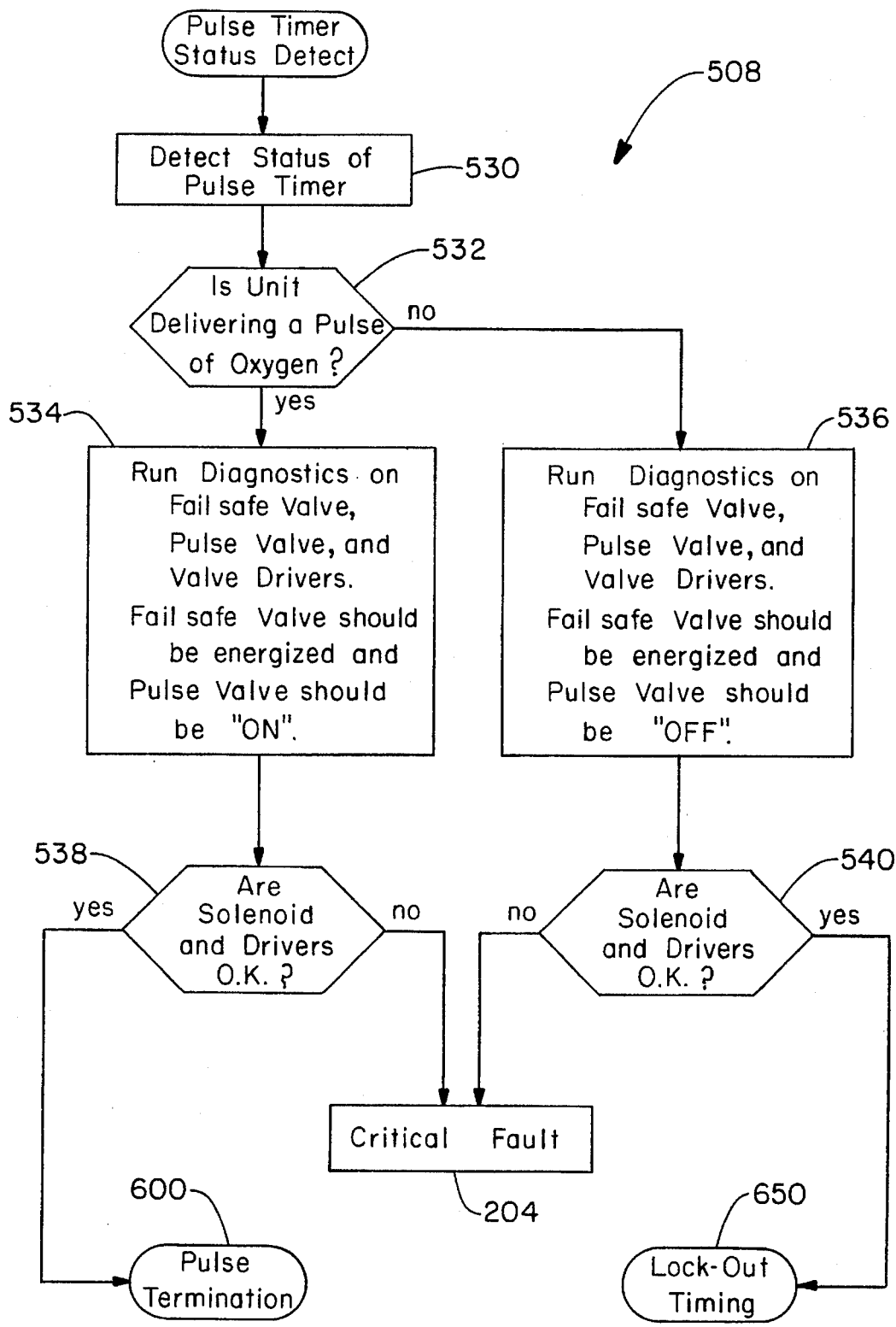
FIG. 9 is a flow chart of the microprocessor control circuit PULSE TIMER STATUS DETECT subroutine.

PULSE TIMER STATUS DETECT 508, shown in FIG. 9, starts by determining if the pulse timer is currently turned on or off at 530. It further checks to see if apparatus 10 is delivering a pulse of oxygen at 532. Whether it is or not, essentially the same test is performed next. In each case diagnostics are run on fail-safe valve 22, pulse dose valve 18, and both valve's driver circuitry. The only difference is that if the unit was delivering oxygen when the diagnostics began, pulse dose valve 18 should be on at 534. If the unit was not delivering oxygen, then pulse dose valve 18 should be off at 536. If the unit was delivering oxygen and the valves and drivers are working at 538, micro-controller 8 calls PULSE TERMINATION 600. If the unit was not delivering oxygen and the valves and drivers are working at 540, micro-controller 8 calls LOCK OUT TIMING 650. If in either case the valves or drivers were not functioning then CRITICAL FAULT 204 is entered and the unit shuts down into its fail-safe mode.

Figure 11:
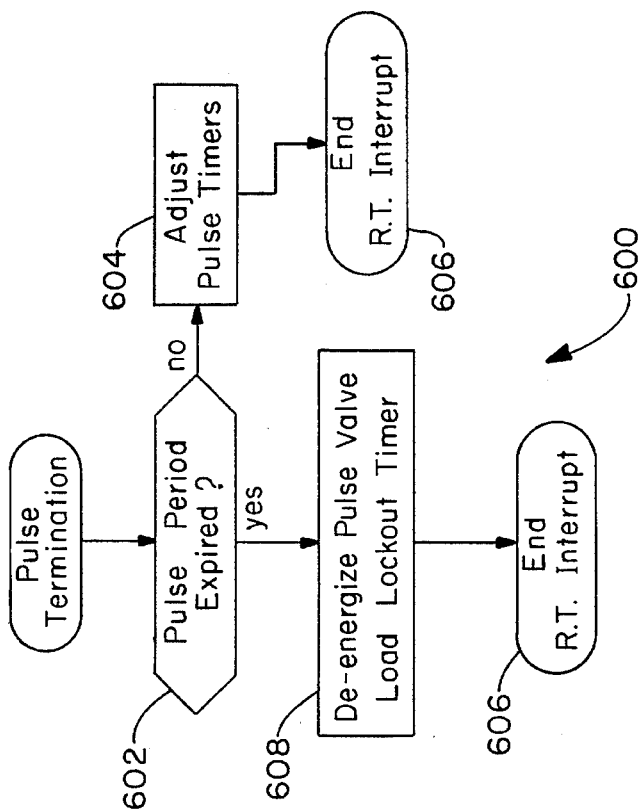
FIG. 11 is a flow chart of the microprocessor control circuit PULSE TERMINATION subroutine.

If apparatus 10 enters PULSE TERMINATION 600, shown in FIG. 11, it first checks to see if the pulse period has expired at 602, and if not it readjusts its internal pulse timers at 604 and exits from the real time interrupt call at 606. If the pulse period did expire at 602, then pulse dose valve 100 is closed and a variable called the "Load Lockout Timer" is initialized at 608 and then the real time interrupt is ended at 606.

Figure 10:
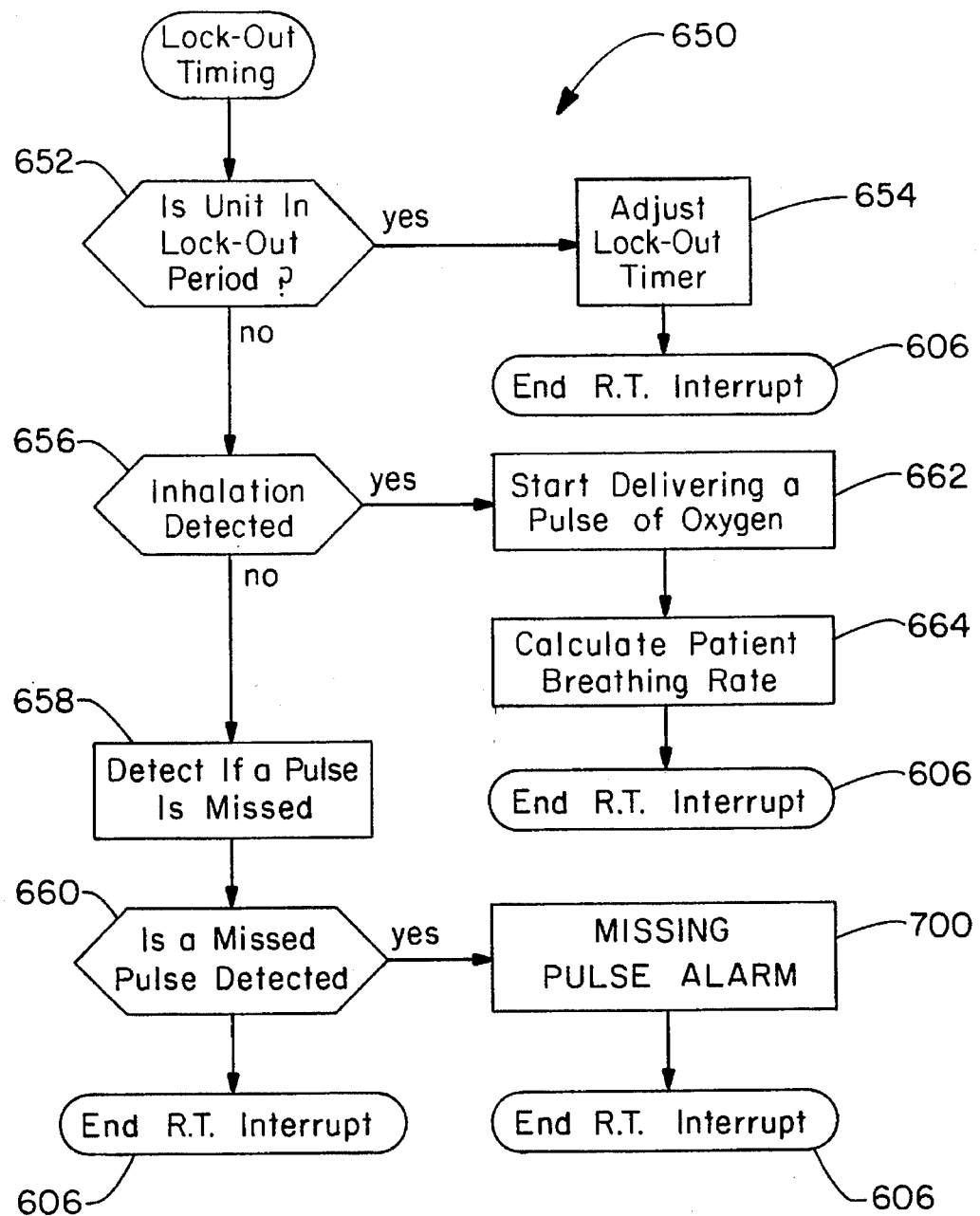
FIG. 10 is a flow chart of the microprocessor control circuit LOCK OUT TIMING subroutine.

If apparatus 10 enters LOCK OUT TIMING 650, as shown in FIG. 10, it first checks to see if a lock out period is currently in progress at 652. If so, the lock out timer is adjusted at 654 and the real time interrupt ends at 606. If the unit was not in a lock out period at 652, then it is determined if patient inhalation has begun. The lock out timer is used to keep the system from interrupting the patient's oxygen supply if the patient is in the middle of inhaling. This feature adds a software fail-safe to ensure that the patient receives all the oxygen necessary and prevents electronic interference and glitches, common to microprocessor technology, from interrupting the patient. If the inhalation phase is detected, the unit begins to deliver a pulse of oxygen to the patient at 662. At this point, apparatus 10 enters the subroutine CALCULATE PATIENT'S BREATHING RATE 654, which uses the detection of inhalation via flow/pressure sensor 100 and clocking signals generated by micro-controller 8. After the patients breathing rate is determined and stored in micro-controller's 8 memory, it returns from the real-time interrupt at 606. If the inhalation phase was not detected at 656, the unit uses the previous measurement of the patients breathing rate to determine if any pulses of oxygen have been missed at 658, which would indicate that the patient has stopped breathing. If a pulse has not been missed at 658, the unit will return from the real-time interrupt at 606. If a pulse was missed, MISSING PULSE ALARM 700 is called. If the unit returns from this subroutine, it will then exit from the real-time interrupt at 606.

Figure 18:
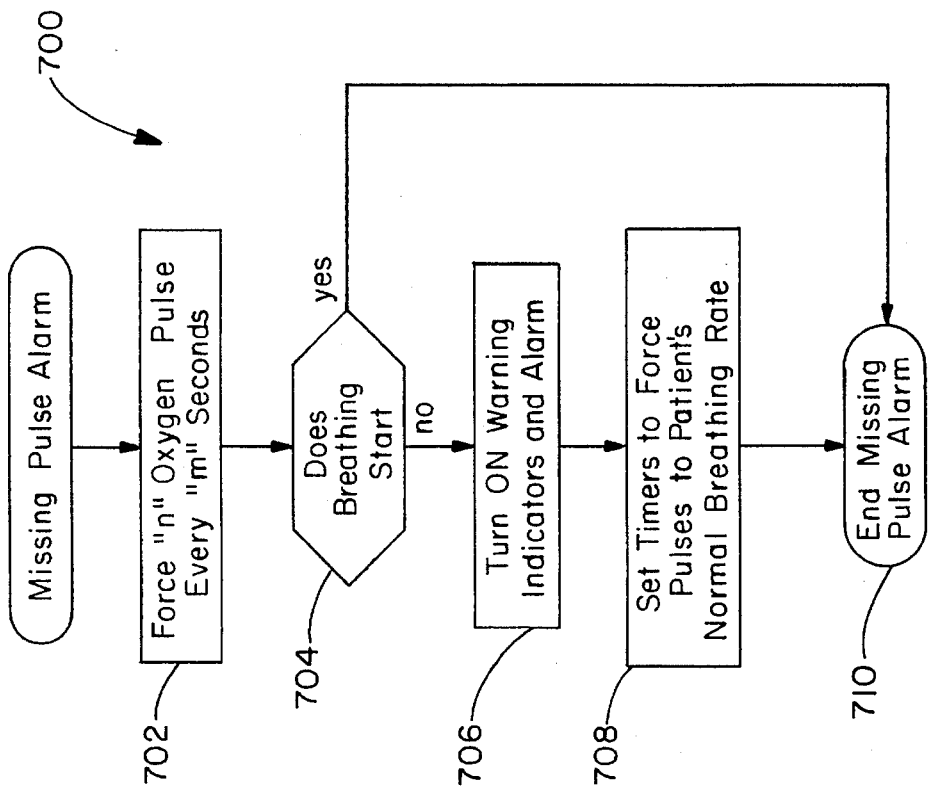
FIG. 18 is a flow chart of the microprocessor control circuit MISSING PULSE ALARM subroutine.

MISSING PULSE ALARM 700, as shown in FIG. 18, begins by forcing a predetermined number of oxygen pulses every "n" seconds at 702, being a preselected value. It then checks to see if the patient has begun to breath on their own at 704. If so the subroutine exits at 710. If not, the unit turns on missing pulse indicator 42 and audible alarm 40. The unit then resets its pulse timers so that the pulse doses of oxygen are delivered at the patient's previously determined normal breathing rate 708 and the subroutine exits at 710.

While the above software operations of a preferred embodiment have been described in detail, it should be noted that due to the nature and versatility of software, the implementation of the subroutine calls may be performed in a variety of fashions contemplated within the invention, and use of the subroutines is also selective and variable. The underlying steps of the process used to implement the pulse dose and conservation delivery of oxygen are the important and novel aspects of the invention. Also, due to the flexibility of computer technology several other functions are contemplated as additional features. For example, a complete breathing rate and alarm condition log may be provided. By adding additional memory to micro-controller 8, a log containing the date of treatment, the length of treatment, the patient's breathing rate over time, the rate of actual oxygen consumption and pressure decrease, the time of any warnings or malfunctions and what they were, and many other valuable information could be provided. Such information could be used for patient or apparatus monitoring and could be stored and retrieved at any time. The retrieval could be to a personal computer via a serial or parallel data link or apparatus 10 could be equipped with a modem or a cellular modem for remote monitoring. This would be highly advantageous today with the trend toward home health care. Instead of incurring the high cost of hospital stays, patients could be monitored at their homes. If critical warnings, such as when the patient stops breathing, are detected micro-controller 8 could automatically dial emergency personnel. This type of instantaneous information management would improve the odds of a patient surviving an emergency.

Micro-controller 8 could also be equipped with additional outputs that simply make or break connections, such as through relays. These could be used to send signals to other medical equipment if certain conditions are established. This would also provide flexibility in that apparatus 10 would be able to interface to currently nonexistent technology that may be developed in the future and that may benefit the patient. Although preferred embodiments of the invention have been described, various modifications would occur to those skilled in the art, and are contemplated in the invention. Accordingly, modifications may be made without departing from the scope of the invention, and it is intended to claim all modifications and variations as fall within the scope of the invention as defined in the appended claims.

What is claimed is:

1. A gas delivery apparatus consisting essentially of
    a gas pressure regulator, having an input and an output, with said input selectively coupled to a gas supply source;
    a pressure sensor coupled to said output of said gas pressure regulator for sensing fluidic supply pressure emitted from said output of said pressure regulator;
    at least one gas valve, having an input and an output, with said input of said at least one gas valve fluidically coupled to said output of said pressure regulator downstream of said pressure sensor;
    a control system for controlling said at least one gas valve and communicating with said pressure sensor; and
    an output port coupled to said output of said at least one gas valve.

2. The gas delivery apparatus as recited in claim 1, further comprising a gas flow selection valve coupled between said pressure regulator and said at least one gas valve to further limit gas supplied to said output port.

3. The gas delivery apparatus as recited in claim 1, further comprising a fluidic switch coupled from said input to said output of said at least one gas valve, allowing said at least one gas valve to be manually overridden to allow gas to be supplied continuously to said output port.

4. The gas delivery apparatus as recited in claim 1, further comprising;
    a second gas valve, having an input and an output, said second gas valve coupled between said output of said at least one gas valve and said output port, said second gas valve controlled by said control system.

5. The gas delivery apparatus as recited in claim 4, wherein said at least one gas valve and said second gas valve each has a common port, a normally-closed port, and a normally-open port, wherein said at least one gas valve and said second gas valve each operate to default to said normally-open port which allows communication of gas between said normally-open port and said common port.

6. The gas delivery apparatus as recited in claim 5, further comprising a gas flow selection valve, having an input and an output, said input of said gas flow selection valve coupled to said output of said pressure regulator and said output of said gas flow selection valve coupled to said second gas valve.

7. The gas delivery apparatus as recited in claim 6, wherein
    said output of said gas flow selection valve is coupled to said normally-open port of said second gas valve,
    said common port of said at least one gas valve is coupled to said normally-closed port of said second gas valve,
    said common port of said second gas valve is coupled to said output port, and
    said normally-closed port of said at least one gas valve is coupled to said output of said pressure regulator.

8. The gas delivery apparatus as recited in claim 2, further comprising a remote gas flow selector, said remote gas flow selector being coupled to said gas flow selection valve and to said control system and operating to adjust the gas flow of said gas flow selection valve.

9. The gas delivery apparatus as recited in claim 1, further comprising a plurality of visual indicators operated by said control system for indicating status conditions of said apparatus.

10. The gas delivery apparatus as recited in claim 1, further comprising an audible transducer electrically coupled to said control system for signalling status conditions of said apparatus.

11. The gas delivery apparatus as recited in claim 1, wherein,
    said control system includes at least one sensor to detect the breathing cycle of a patient to whom gas is delivered by means of said output port, and controls operation of said at least one gas valve to supply gas to said output port.

12. The gas delivery apparatus as recited in claim 11, wherein,
    said control system controls operation of said at least one gas valve to supply gas to said output port at predetermined intervals.

13. The gas delivery apparatus as recited in claim 12, wherein,
    said gas is supplied to said output port during an inhalation phase of said breathing cycle.

14. The gas delivery apparatus as recited in claim 12, wherein,
    said gas is supplied to said output port substantially continuously during said breathing cycle.

15. The gas delivery apparatus as recited in claim 11, wherein,
    said control system controls operation of said at least one gas valve to supply gas to said output port in a predetermined amount.

16. The gas delivery apparatus as recited in claim 11, wherein,
    said control system monitors said breathing cycle and controls operation of said at least one gas valve to supply gas to said output port upon detecting an abnormality in said breathing cycle.

17. A method of delivering a respiratory gas to a patient comprising the steps of:
    providing a portable gas delivery system comprising a gas pressure regulator having an input and an output, with the input selectively coupled to a gas supply source, a pressure sensor coupled to said output of the gas pressure regulator for sensing fluidic supply pressure emitted from the output of the pressure regulator, at least one gas supply valve having an input and output, with the input of the at least one gas valve fluidically coupled to the output of the pressure regulator downstream of the pressure sensor, a control system for controlling the at least one gas valve and communicating with the pressure sensor, and an output port coupled to the output of the at least one gas valve:
    supplying a gas at a controllable pressure and predetermined flow rate from said gas supply source to the at least one gas supply valve;
    monitoring the breathing cycle of a patient;
    measuring the volume of said supply gas through said at least one gas supply valve; and controlling said at least one gas supply valve to supply a predetermined volume of gas to said patient at predetermined times according to said breathing cycle.

18. The method as in claim 17, further comprising the steps of:

monitoring the breathing pressure of said patient;

supplying gas to said patient upon detecting a decrease in pressure due to inhalation, and stop the supply of gas upon detecting a return to ambient or a greater pressure due to the inhalation cycle ending.

19. The method as in claim 17, further comprising the steps of:

setting said supply gas to a constant flow rate such that the volume of gas needed in a breath can be delivered within approximately half of a inhalation cycle;

measuring the actual pressure of said supply gas;

calculate the time period necessary to provide said supply gas for in order to deliver the desired volume of said supply gas at a predetermined nominal pressure;

calculate the compensation time period to compensate for the difference in said predetermined nominal pressure and said actual pressure by determining the difference in said pressures and adding this value to said predetermined nominal pressure; and deliver gas supplied at the actual pressure for a time period equal to said predetermined nominal pressure time period plus said compensation time period.

20. The method as in claim 17, further comprising the steps of:

detecting the start of a plurality of inhalation cycles and calculating a breathing rate;

calculating a time period in which said inhalation cycle must begin based on said breathing rate;

comparing the lapse of time since said previous inhalation cycle to determine if said inhalation cycle has not begun within said time period;

supplying gas upon detecting that said inhalation cycle has not begun within said time period.

21. A portable gas delivery apparatus comprising:

a gas pressure regulator, having an input and an output, with said input selectively coupled to a gas supply source;

a pressure sensor coupled to said output of said gas pressure regulator for sensing fluidic supply pressure emitted from said output of said pressure regulator;

at least one gas valve, having an input and an output, with said input of said at least one gas valve fluidically coupled to said output of said pressure regulator downstream of said pressure sensor;

a control system for controlling said at least one gas valve and communicating with said pressure sensor; and an output port coupled to said output of said at least on gas valve;

wherein the gas delivery apparatus is portable with a user.

22. The apparatus of claim 21 wherein said gas supply source is a portable pressurized tank.

23. The apparatus of claim 21, further comprising a gas flow selection valve coupled between said pressure regulator and said at least on gas valve to further limit gas supplied to said output port.

24. The apparatus as recited in claim 21, further comprising a fluidic switch coupled from said input to said output of said at least one gas valve, allowing said at least one gas valve to be manually overridden to allow gas to be supplied continuously to said output port.

25. The apparatus of claim 21, further comprising:

a second gas valve, having an input and an output, said second gas valve coupled between said output of said at least one gas valve and said output port, said second gas valve controlled by said control system.

26. The apparatus of claim 25, wherein said at least on gas valve and said second gas valve each has a common port, a normally-closed port, and a normally-open port, wherein said at least one gas valve and said second gas valve each operated to default to said normally-open port which allows communication of gas between said normally-open port and said common port.

27. The apparatus of claim 26, further comprising a gas flow selection valve, having an input and an output, said input of said gas flow selection valve coupled to said output of said pressure regulator and said output of said gas flow selection valve coupled to said second gas valve, wherein said output of said gas flow selection valve is coupled to said normally-open port of said second gas valve, said common port of said at least one gas valve is coupled to said normally-closed port of said second gas valve;

said common port of said second gas valve is coupled to said output port; and said normally-closed port of said at least one gas valve is coupled to said output of said pressure regulator.

28. The apparatus of claim 23, further comprising a remote gas flow selector, said remote gas flow selector being coupled to said gas flow selection valve and to said control system and operating to adjust the gas flow of said gas flow selection valve.

29. The apparatus of claim 21, further comprising at least one indicator operated by said control system for indicating at least on status condition of said apparatus.

30. The apparatus of claim 21, wherein said control system includes at least one sensor to detect the breathing cycle of a patient to whom gas is delivered by means of said output port, and controls operation of said at least one gas valve to supply gas to said output port.

31. The apparatus of claim 21, wherein said control system controls operation of said at least one gas valve to supply gas to said output port at predetermined intervals.

32. The apparatus of claim 21, wherein said control system includes at least one sensor to detect the breathing cycle of a patient, and controls operation of said at least one gas valve, wherein said gas is supplied to said output port during an inhalation phase of said breathing cycle.

33. The apparatus of claim 21, wherein said control system controls operation of said at least one gas valve to supply gas to said output port in a predetermined amount.

34. The apparatus of claim 21, wherein said control system monitors said breathing cycle and controls operation of said at least one gas valve to supply gas to said output port upon detecting an abnormality in said breathing cycle.

* * * * *